(12) United States Patent
Bishop

(10) Patent No.: US 6,979,445 B2
(45) Date of Patent: Dec. 27, 2005

(54) METHOD FOR TREATING VON WILLEBRAND'S DISEASE

(75) Inventor: Paul D. Bishop, Fall City, WA (US)

(73) Assignee: Zymogenetics, INC, Seattle, WA (US)

( * ) Notice: Subject to any disclaimer, the term of this patent is extended or adjusted under 35 U.S.C. 154(b) by 0 days.

(21) Appl. No.: 10/468,113

(22) PCT Filed: Feb. 7, 2002

(86) PCT No.: PCT/US02/03742

§ 371 (c)(1),
(2), (4) Date: Aug. 15, 2003

(87) PCT Pub. No.: WO02/067980

PCT Pub. Date: Sep. 6, 2002

(65) Prior Publication Data

US 2004/0067230 A1    Apr. 8, 2004

Related U.S. Application Data

(60) Provisional application No. 60/270,460, filed on Feb. 21, 2001.

(51) Int. Cl.[7] ............... A61K 38/11; A61K 38/36; A61K 38/45; A61P 7/04
(52) U.S. Cl. ............... 424/94.5; 514/8; 514/21
(58) Field of Search ............... 424/94.1, 94.5; 435/193, 232; 514/8, 21; 530/381, 395

(56) References Cited

FOREIGN PATENT DOCUMENTS

WO    WO 01/85198 A * 11/2001

OTHER PUBLICATIONS

Nilsson et al. Characteristics Of The Factor-VIII Protein And Factor-XIII In Various Factor-VIII Concentrates. Scandinavian Journal Of Haemotology. 1980, vol. 24, No. 4, pp. 340-349.*
Moro et al. Statistic Considerations In The Treatment . . . Rivista Italiana Di Stomatologia. Jul.-Aug. 1983, vol. 72, Nos. 7-8, pp. 589-592.*
Beersmh et al. Merck Manual of Diagnosis And Therapy, 17th ed. 1999, pp. 888-889.*
Berry. Use Of DDAVP And Cryoprecipitate In Mild To Moderate Haemophilia A And Von Willebrands Disease. Progress In Clinical And Biological Research. 1990, vol. 324, pp. 269-278.*

* cited by examiner

*Primary Examiner*—Jeffrey Edwin Russel
(74) *Attorney, Agent, or Firm*—Len S. Smith; Reza Green; Richard Bork

(57) ABSTRACT

Use of factor XIII for treating von Willebrand's disease. A patient having von Willebrand's disease is treated by administering factor XIII generally in conjunction with factor VIII concentrate, 1-desamino-8-D-arginine vasopressin (DDAVP) or desmopressin.

6 Claims, No Drawings

METHOD FOR TREATING VON WILLEBRAND'S DISEASE

The present application is a 35 U.S.C. 371 application of PCT/US02/03742 filed Feb. 7, 2002, which claims the benefit of U.S. Provisional Application Ser. No. 60/270,460 filed Feb. 21, 2001, both of which are incorporated by reference herein.

BACKGROUND OF THE INVENTION

Von Willebrand's disease (vWD) is the most common inherited bleeding disorder and may occur in as many as 1 in 800 individuals. The von Willebrand factor (vWF) is heterogeneous multimeric plasma glycoprotein with two major functions. It facilitates platelet adhesion under conditions of high shear stress by linking platelet membrane receptors to vascular subendothelium. It also serves as the plasma carrier for factor VIII. The normal plasma level of vWF is 10 mg/L. The vWF activity is distributed among a series of plasma multimers with estimated molecular weights ranging from 400,000 to over 20 million. A single large vWF precursor subunit is synthesized in endothelial cells and megakaryocytes, where it is cleaved and assembled into the disulfide-linked multimers present in plasma, platelets, endothelial cells, and in the basement membrane of blood vessels. All of these pools of vWF contribute to the protein's main function, which is to promote attachment of platelets to areas of vessel injury. To optimize the availability of vWF at the site of injury, a highly active form of the protein is stored in secretory granules of platelets and of endothelial cells. When these cells sense tissue injury (e.g. by contact with thrombin) they instantly mobilize the stored vWF. The released vWF binds to glycoprotein Ib (GPIb) on the platelet surface and to components of the basement membrane, forming a bridge that can withstand high sheer stress of blood flow. VWF is necessary for this initial attachment of platelets to the injured area. Together with other adhesive proteins, such as fibrinogen, fibronectin, and thrombospondin, vWF interacts with the GPIIb/IIIa on activated platelets and contributes to platelet spreading and aggregation.

A modest reduction in plasma vWF concentration, or a selective loss in the high-molecular weight multimers, decreases platelet adhesion and causes clinical bleeding. Although vWD is heterogeneous, there are certain clinical features that are common to all the syndromes. With one exception (type III disease), all forms are inherited as autosomal dominant traits and affected patients are heterozygous with one normal and one abnormal vWF allele. In mild cases, bleeding occurs only after surgery or trauma. There are three major types of vWD. Patients with type I disease, the most common abnormality, have a mild to moderate decrease in plasma vWF. In the milder cases, although hemostasis is clearly impaired, the vWF level is just below the lower limit of normal, less than 5 mg/L. In type I disease, there is a parallel decrease in vWF antigen, factor VIII activity, and ristocetin cofactor activity, with a normal spectrum of multimers detected by sodium dodecyl sulfate (SDS)-agarose gel electrophoresis. Cultured endothelial cells derived from the umbilical cords of patients with vWD synthesize and secrete reduced quantities of vWF multimer and have a two- to fourfold reduction in vWF mRNA.

The variant forms of vWD (type II disease), which are much less common, are characterized by normal or near-normal levels of a dysfunctional vWF. Patients with the type IIa variant of vWD have a deficiency in the high- and medium molecular-weight forms of vWF multimer detected by SDS-agarose electrophoresis. This is due either to an inability to secrete the high-molecular-weight vWF multimets or to proteolysis of the multimers soon after they leave the endothelial cell and enter the circulation. The quantity of vWF antigen and the amount of associated factor VIII are usually normal. In the type IIb variant, there is also a loss in high-molecular-weight multimers. However, in type IIb disease, it is due to the inappropriate binding of vWF to platelets. This forms intravascular platelet aggregates that are rapidly cleared from the circulation, causing mild, cyclic thrombocytopenia.

Approximately 1 in 1 million individuals have a very severe form of vWD that is phenotypically recessive (type III disease). Type III patients are usually the offspring of two parents with mild type I disease. However, in many cases, the parents are very mildly affected or are asymptomatic. Type III patients may inherit a different abnormality from each parent (a doubly heterozygous or compound heterozygous state) or be homozygous for a single defect. Type III patients have severe mucosal bleeding, no detectable vWF antigen or activity, and may have sufficiently low factor VIII that they have occasional hemarthroses like mild hemophiliacs.

Prior art treatment of vWD depends on the symptoms and the underlying type of disease. One type of treatment involves the use of cryoprecipitate, a plasma fraction enriched in vWF, or factor VIII concentrates, which retain high-molecular-weight vWF multimers (HUMATE-P®, KOATE HS®). A second therapeutic option, which avoid the use of plasma is use of 1-desamino-8-D-arginine vasopressin (DDAVP), or desmopressin.

However, there are times when treating such patients with the above-described therapeutic agents produces less than satisfactory results, and hemorrhaging continues. Thus, there is a need to develop additional therapies for treating vWD.

DESCRIPTION OF THE INVENTION

The present invention fills this need by administering factor XIII to patients with vWD, preferably in conjunction with either factor VIII concentrates, plasma cryoprecipitate enriched in vWF, DDAVP or desmopressin acetate.

Diagnosis of Von Willebrand's Disease

Once a bleeding disorder has been determined to be present, the physician must determine what is the cause of the disorder. Although a prolonged bleeding time is the hallmark of vWD, this laboratory finding is not specific for vWD. Thus, the diagnosis of vWD is definitively established by means of additional laboratory tests. See Triplett, DA: Laboratory Diagnosis of von Willebrand's Disease, *Mayo Clin. Proc.* 66:832 (1991). These usually include measurements of the amount of vWF protein present in plasma, the functional activity of the vWF, and the procoagulant activity of the associated factor VIII.

Treatment of Von Willebrand's Disease with Factor VIII and Factor XIII

The method of the present invention improves upon the above-described treatment of von Willebrand's disease by administering factor XIII in conjunction with cryoprecipitate enriched in vWF, factor VIII concentrate, DDAVP or desmopressin acetate. The factor XIII can be administered at any time alone or at the same time as the other therapies either to stop a hemorrhage or for prophylaxis.

Factor XIII, also known as fibrin-stabilizing factor, circulates in the plasma at a concentration of about 20 mg/ml. The protein exists in plasma as a tetramer comprised of two A subunits and two B subunits. Each subunit has a molecular weight of 83,000 Da, and the complete protein has a molecular weight of approximately 330,000 Da. Factor XIII catalyzes the cross-linkage between the γ-glutamyl and ε-lysyl groups of different fibrin strands. The catalytic activity of factor XIII resides in the A subunits. The B subunits act as carriers for the A subunits in plasma factor XIII. Recombinant factor XIII can be produced according to the process described in European Patent No. 0 268 772 B1. The level of factor XIII in the plasma can also be increased by administering a factor XIII concentrate derived from human placenta called FIBROGAMMIN® (Aventis Corp.) or by administration of recombinant factor XIII.

Administration of factor XIII to a subject is preferably intravenous. When administering therapeutic proteins by injection, the administration may be by continuous infusion or by single or multiple boluses. A pharmaceutical composition comprising factor XIII can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. A suitable pharmaceutical composition of factor XIII will contain 1 mM EDTA, 10 mM Glycine, 2% sucrose in water. An alternative formulation will be a factor XIII composition containing 20 mM histidine, 3% wt/volume sucrose, 2 mM glycine and 0.01% wt/vol. polysorbate, pH 8. The concentration of factor XIII should preferably be 1–10 mg/ml, more preferably about 5 mg/mL.

Other suitable carriers are well known to those in the art. See, for example, Gennaro (ed.), *Remington's Pharmaceutical Sciences*, 19th Edition (Mack Publishing Company 1995).

Factor XIII can be administered intravenously, intramuscularly or subcutaneously to treat vWD. The levels of factor XIII in an individual can be determined by assays well known in the art such as the BERICHROM® F XIII assay (Dade Behring Marburg GmbH, Marburg, Germany). The normal adult has an average of about 45 ml of plasma per kg of body weight. Each liter of blood has 1000 units (U) of factor XIII. A dose of 0.45 U/kg would raise the level of factor XIII by about 1% compared to normal. One unit of factor XIII is about 10 micrograms (mcg) of recombinant factor XIII, which contains only the dimerized, 'A' subunit.

Thus, to raise the level of factor XIII by 1%, one would administer about 4.5 mcg of the A2 subunit per kilogram weight of the individual. So to raise the level 30% of normal, one would administer 13.5 U/kg. For a 75 kg individual this would be about 1,012.5 U. Some patients may have consumptive coagulopathies that involve factor XIII losses. In such cases, a higher dosing (e.g., 1–2 U/kg-%) or multiple dosing of factor XIII (e.g., 1–2 U/kg-%-day) may be required.

Factor VIII concentrate is produced by a number of companies including HEMAFIL M (human, plasma-derived) produced by Baxter Healthcare Corp.; HUMATE-P CONCENTRATE® (human, plasma-derived) produced by Centeon L.L.C.; KOATE-DVI® (human, plasma-derived) produced by Bayer Biological; KOATE HP (human, plasma-derived) produced by Bayer Biological; MONOCLATE-P® (human, plasma-derived) produced by Centeon L.L.C.

Desmopressin acetate and DDAVP are produced by Rhône-Poulenc Rorer, Collegeville, Pa., by Ferring Pharmaceutical, Tarrytown, N.Y., and by Centeon, King of Prussia Pa.

What is claimed is:

1. A method for treating von Willebrand's disease comprising administering to an individual having said disease an amount of recombinant factor XIII effective to treat the disease.

2. The method of claim 1, wherein the factor XIII is administered to said individual during a bleeding episode.

3. A method for treating von Willebrand's disease comprising administering to an individual having said disease an effective combination of recombinant factor XIII In conjunction with and one or more additional therapeutic agents, wherein said the one or more additional therapeutic agents agent are is selected from the group consisting of factor VIII concentrate, plasma cryoprecipitate, desmopressin and 1-desamino-8-D-arginine vasopressin (DDAVP).

4. The method of ciaim 3, wherein the factor XIII is administered prior to the administration of the one or more additional therapeutic agent agents.

5. The method of claim 3, wherein the factor XIII is administered after the administration of the one or more additional therapeutic agent agents.

6. The method of claim 3, wherein the factor XIII is administered simultaneously with the administration of the one or more additional therapeutic agent agents.

* * * * *